(12) United States Patent
Fischer et al.

(10) Patent No.: US 11,045,232 B2
(45) Date of Patent: Jun. 29, 2021

(54) INSTRUMENT FOR GUIDING A ROD INTO AN IMPLANT HOLDER

(71) Applicant: Aesculap AG, Tuttlingen (DE)

(72) Inventors: Kay Fischer, Tuttlingen (DE); Sven Krüger, Trossingen (DE)

(73) Assignee: AESCULAP AG, Tuttlingen (DE)

( * ) Notice: Subject to any disclaimer, the term of this patent is extended or adjusted under 35 U.S.C. 154(b) by 333 days.

(21) Appl. No.: 16/074,315

(22) PCT Filed: Feb. 2, 2017

(86) PCT No.: PCT/EP2017/052234
§ 371 (c)(1),
(2) Date: Jul. 31, 2018

(87) PCT Pub. No.: WO2017/134154
PCT Pub. Date: Aug. 10, 2017

(65) Prior Publication Data
US 2020/0383706 A1     Dec. 10, 2020

(30) Foreign Application Priority Data

Feb. 2, 2016   (DE) ...................... 10 2016 101 822.8
Apr. 11, 2016  (DE) ...................... 10 2016 106 608.7

(51) Int. Cl.
*A61B 17/70*      (2006.01)
*A61B 17/00*      (2006.01)

(52) U.S. Cl.
CPC ...... *A61B 17/7086* (2013.01); *A61B 17/7032* (2013.01); *A61B 2017/00477* (2013.01)

(58) Field of Classification Search
CPC ............ A61B 17/7086; A61B 17/7032; A61B 17/7085; A61B 17/708; A61B 17/7002;
(Continued)

(56) References Cited

U.S. PATENT DOCUMENTS 8,317,796 B2   11/2012   Stihl et al.
8,906,034 B2   12/2014   Gleeson et al.
(Continued)

FOREIGN PATENT DOCUMENTS

CN   102149344 A   8/2011
CN   104883990 A   9/2015
(Continued)

OTHER PUBLICATIONS

German Search Report for German Application No. 10 2016 101 822.8, dated Aug. 24, 2016, with partial translation—15 pages.
(Continued)

*Primary Examiner* — Pedro Philogene

(57) ABSTRACT

An instrument for guiding a rod into a holder of an implant, in particular a pedicle screw, includes a coupling unit for coupling the instrument to the implant, in particular a head of the pedicle screw, a threaded rod that can be positioned in the axial direction relative to the coupling unit, and at least one internally threaded segment that is arranged in an axially fixed manner relative to the coupling unit, and can be positioned in a radial direction relative to the threaded rod, and prestressed toward the threaded rod by a prestressing element applying a radial force. The internally threaded segment can be brought into engagement with, and disengaged from, the male thread of the threaded rod by radial positioning. Thread flanks of the threaded rod and thread flanks of the internally threaded segment face each other and are each formed with an undercut.

15 Claims, 13 Drawing Sheets

Figure 1:
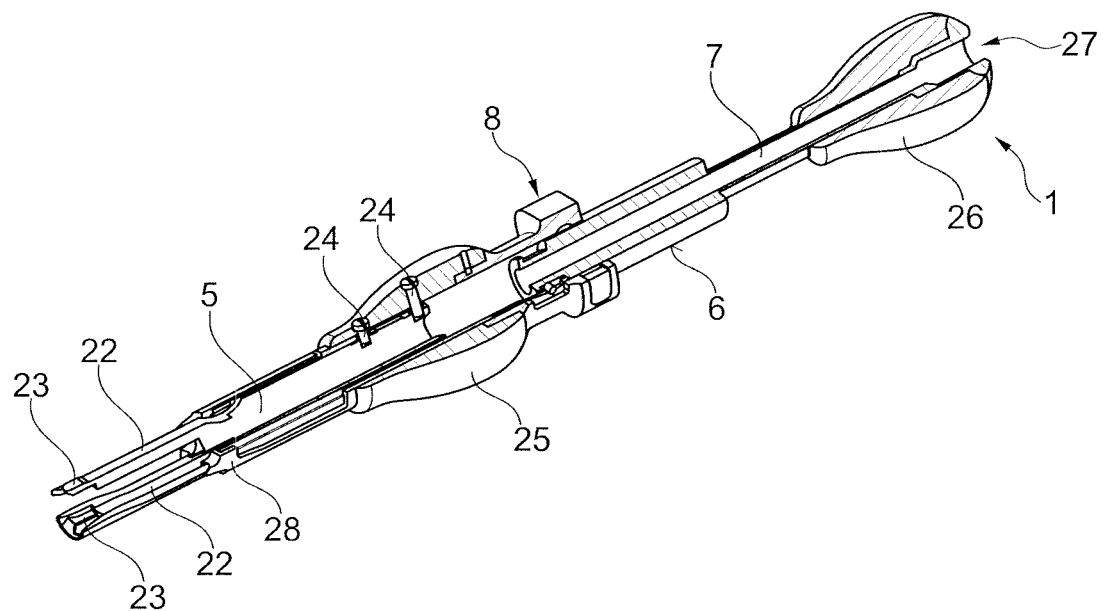

(58) Field of Classification Search
CPC ............ A61B 17/7037; A61B 17/7091; A61B 17/7076; A61B 17/7082; A61B 17/7074; A61B 2017/00477
USPC ........... 606/86 A, 96, 99, 103, 100, 250–279
See application file for complete search history.

(56) References Cited

U.S. PATENT DOCUMENTS

| | | |
|---|---|---|
| 9,289,249 B2 | 3/2016 | Ramsay et al. |
| 9,433,445 B2 | 9/2016 | Ramsay et al. |
| 9,918,752 B2 | 3/2018 | Hennard et al. |
| 2002/0026194 A1 | 2/2002 | Morrison et al. |
| 2002/0138076 A1 | 9/2002 | Biedermann et al. |
| 2007/0185375 A1 | 8/2007 | Stad et al. |
| 2008/0228233 A1 | 9/2008 | Hoffman et al. |
| 2008/0319477 A1 | 12/2008 | Justis et al. |
| 2010/0121385 A1 | 5/2010 | Blain et al. |
| 2012/0191144 A1* | 7/2012 | Peultier ............ A61B 17/7086 606/86 A |
| 2012/0253413 A1 | 10/2012 | Runco et al. |
| 2014/0276894 A1* | 9/2014 | Ramsay ............ A61B 17/7076 606/104 |
| 2014/0276895 A1 | 9/2014 | Jackson et al. |
| 2015/0100097 A1 | 4/2015 | Barrus |
| 2015/0100098 A1 | 4/2015 | Moore |
| 2016/0206354 A1* | 7/2016 | Mladenov .......... A61B 17/7086 |
| 2017/0252074 A1* | 9/2017 | Semingson ........ A61B 17/7085 |
| 2019/0125417 A1 | 5/2019 | Fischer |

FOREIGN PATENT DOCUMENTS

| | | |
|---|---|---|
| CN | 105188583 A | 12/2015 |
| DE | 19912364 A1 | 10/2000 |
| DE | 102011103252 A1 | 11/2012 |
| EP | 1219255 A1 | 7/2002 |
| EP | 2878276 A2 | 6/2015 |
| JP | 2015515346 A | 5/2015 |
| JP | 2016511064 A | 4/2016 |
| WO | 2013009493 A2 | 1/2013 |
| WO | 2015054200 A1 | 4/2015 |

OTHER PUBLICATIONS

International Search Report and Written Opinion for International Application No. PCT/EP2017/052234, dated Apr. 12, 2017—9 pages.
Chinese Office Action received in Application No. 201780009644.9 dated Aug. 26, 2020, 15 pages.
Chinese Search Report received in Application No. 201780009644.9 dated Aug. 19, 2020, 5 pages.
Office Action received in Chinese Application No. 201780009644.9 dated Mar. 5, 2021, with translation, 17 pages.
Office Action received in Japanese Application No. 2018-553457 dated Apr. 14, 2021, with translation, 14 pages.

* cited by examiner

INSTRUMENT FOR GUIDING A ROD INTO AN IMPLANT HOLDER

RELATED APPLICATIONS

This application is the United States national phase entry of International Application No. PCT/EP2017/052234, filed Feb. 2, 2017, which claims the benefit of priority of German Application No. 10 2016 101 822.8, filed Feb. 2, 2016, and which also claims the benefit of German Application No. 10 2016 106 608.7, filed Apr. 11, 2016. The contents of International Application No. PCT/EP2017/052234, German Application No. 10 2016 101 822.8, and German Application No. 10 2016 106 608.7 are incorporated by reference herein in their entireties.

FIELD

The present invention relates to an instrument for the relative positioning and/or guiding and/or inserting of a rod into a seat of an implant, in particular of a pedicle screw, comprising a coupling unit for coupling the instrument to the implant, in particular to a head of the pedicle screw, a threaded rod which is provided with a male thread and can be positioned in the axial direction in relation to the coupling unit, and at least one internally threaded segment which is arranged in an axially fixed manner in relation to the coupling unit, can be positioned in the radial direction relative to the threaded rod and is prestressed toward the threaded rod by a prestressing element applying a radial force, wherein the internally threaded segment can be brought into engagement with, and disengaged from, the male thread of the threaded rod by virtue of radial positioning.

BACKGROUND

Such instruments are used, for example, in open spine operations to create a fixed or rigid connection between pedicle screws screwed into different vertebrae using a rod. The instrument is used to insert rods, by means of which adjacent pedicle screws are fixed relative to each other, into their respective tulip and to hold them in this position so that the rod can be secured there with a set screw.

In cases where the distance between the rod and the tulip is small, a rod pusher, a simple lever instrument, is usually used to push the rod into the tulip. In cases where the rod is placed far above and spaced from the tulip, e.g. due to spondylolisthesis (slipping vertebra), large forces may be required to force the rod into the tulip or to pull a slipped vertebral body into the desired position. Usually, rod persuaders are used for this purpose.

An instrument with a pistol grip and ratchet mechanism is known, in which the ratchet serves to fix a distance covered during inserting the rod. With this instrument, forces of medium size can be transmitted. However, it is a disadvantage that no stepless adjustment is possible due to the ratchet mechanism.

With another known instrument, the rod is positioned toward a pedicle screw head exclusively by screw actuation of the instrument, which is thus capable of applying extremely high forces through its thread. Furthermore, an infinitely variable adjustment is possible. If the thread of a rod persuader is self-locking, any position can be held. The disadvantage here is an elaborate and laborious adjustment over long advancement distances.

Finally, a rod persuader with pliers design is known. Due to its multiple transmission, this instrument can travel a long distance when inserting the rod, but is not capable of transmitting such high forces as a rod persuader described above.

The functional principle of the three types mentioned above is similar. One part of the instrument grips the head of a pedicle screw and another part of the instrument rests on a rod to be pressed into the head. The two parts are approximated by one of the mechanisms described above, so that the rod is pressed into the tulip of the pedicle screw head or the screw is pulled towards the rod.

A well-known screw-actuated instrument has an implant holder, a threaded sleeve and a front handle. The implant holder, the threaded sleeve and the handle are arranged or designed to be rotationally and axially fixed to each other. The instrument also comprises a rod pusher and a threaded rod, which are also axially fixed but can rotate relative to each other. Both components are mounted in the instrument so that they can be displaced relative to the implant holder. The threaded rod is provided with a handle at its distal end facing away from the rod pusher and is in engagement with the threaded sleeve. It can therefore be screwed into and out of the threaded sleeve by turning the handle. A translation performed in this way is transferred to the rod pusher as a result of the coupling with the rod pusher described above, but the rod pusher does not rotate. As a result, the implant holder and the rod pusher are axially positioned relative to each other by the threaded rod being screwed in and out of the threaded sleeve.

The possible relative axial positioning of the implant holder and the rod pusher determines the distance over which a rod can be pressed into a pedicle screw tulip by means of the instrument. Usually, this distance is larger than 25 mm, e.g. 45 mm. Depending on the thread pitch, a corresponding number of turns is required to press the rod into the tulip. It is a disadvantage that the processes of turning, re-gripping and continuing the turning required for this are tedious and time-consuming and delay the operation process, especially since this procedure may have to be repeated for several pedicle screws.

A known solution to this problem is, for example, a latching mechanism disclosed in US 2015/0100097 A1 or US 2015/0100098 A1. According to these documents, a threaded rod engages in a spring-mounted threaded shell or thread section that can be positioned relatively in the radial direction. With axial pressure on the threaded rod, the threaded shell/the thread section shifts against the spring preload in radial direction (is deflected), so that the threaded rod can be pushed forward in axial direction without screw movement until a counterpressure exerted by the rod becomes too high. From this point on, further axial positioning can be achieved by means of a screwing process, whereby high forces can be transmitted to the rod. As soon as the rod has reached the desired end position, a set screw is screwed into the tulip and the rod is fixed in this way. The threads are released from each other and brought out of engagement by pressing a release button which is operatively connected to the threaded shell or the thread section. The threaded rod is thus released and can be withdrawn. The advantages of this mechanism are largely fatigue-free work and time savings, since the entire axial positioning does not have to be carried out by a screwing process. However, since these instruments are able to exert compressive forces of several 1000 N, it is a disadvantage that decoupling the threaded rod and threaded shell under pressure presents a risk of injuring surrounding structures or surgical staff.

SUMMARY

Against this background, the present invention is based on the task of providing an instrument for the relative positioning, guiding and insertion of a rod into a holder of an implant, in particular of a pedicle screw, with which high compressive forces can be transferred between rod and implant, and which is also suitable for large initial distances between rod and implant. The instrument should allow an easy-to-handle and safe quick adjustment both during advancing and when releasing, so that endangering structures adjacent to the instrument and injury to surgical staff is excluded or at least minimized. Furthermore, the instrument should be easy to disassemble for cleaning purposes, but unintentional disassembly should always be safely avoided.

According to the present invention, this object is achieved by an instrument for relative positioning and/or guiding and/or inserting a rod, for example a vertebral rod, into a holder of an implant, in particular of a pedicle screw, for example into a head of a pedicle screw, comprising a coupling unit for an (axially fixed) coupling of the instrument with the implant or with an implant holder or with the pedicle screw or with the pedicle screw head, a threaded rod provided with a male thread and positionable in the axial direction relative to the coupling unit and at least one internally threaded segment arranged in an axially fixed manner in relation to the coupling unit, which can be positioned in the radial direction relative to the threaded rod and is prestressed toward the threaded rod by a prestressing element applying a radial force, wherein the internally threaded segment can be brought into engagement or disengaged from the male thread of the threaded rod by radial positioning, which instrument is characterized in that thread flanks of the threaded rod and thread flanks of the internally threaded segment, which face each other, are each formed with an undercut.

Directional information used in the description of the invention, such as axial, radial and tangential, are related to the threaded rod and its orientation. The terms "proximal" and "distal" refer to the working area of the instrument, i.e. the trunk of a patient. In this sense, distal means "away from the patient's trunk", while proximal means "located towards the patient's trunk" or "extending towards the patient's trunk". If the instrument is used as intended, its longitudinal axis, i.e. also the longitudinal axis of the threaded rod, is essentially aligned in the direction of the longitudinal axis of a pedicle screw. It can therefore be said that both the instrument and the threaded rod have a proximal and a distal end.

When the internally threaded segment is positioned in the radial direction on the threaded rod, hereinafter also referred to as the first position, the male thread of the threaded rod and the internal thread of the internally threaded segment are in engagement with each other. When the internally threaded segment is positioned radially away from the threaded rod, hereinafter also referred to as the second position, they are disengaged. In the second position, the threaded rod can therefore be freely positioned in axial direction relative to the internally threaded segment, i.e. can be axially positioned in both proximal and distal directions, in particular by user action. In the first position, the threaded rod cannot be freely positioned axially relative to the internally threaded segment at least in one axial direction, as according to the invention the thread flanks of the threaded rod and the thread flanks of the internally threaded segment, which face each other, each have an undercut. The opposite thread flanks of the threaded rod and the internally threaded segment are preferably designed with a standard positive flank angle and without undercut.

An undercut of a thread flank in the sense of the invention is to be understood as the formation of a thread face in which a thread flank has an outer region in the radial direction which projects in the axial direction in relation to a radially inner region of the same thread flank. This may be the case, for example, if a rear-grip or groove is machined in a thread flank, or the angle of inclination a of a flank is negative (with a conventional metric thread, the angle of inclination of each flank is positive).

As a result of the undercut, the male thread of the threaded rod and the internal thread of the internally threaded segment are interlocked when engaged. If there is a pressure on the threaded rod which acts in the axial direction such that the undercut thread flanks of the threaded rod and the internally threaded segment are pressed against each other, a displacement of the internally threaded segment in the radial direction is therefore not possible. The thread is secured and inhibited, so to speak.

The "normal" thread flanks of the threaded rod and the internally threaded segment which are opposite the undercut thread flanks can act in the sense of the invention as an inclined plane or a deflection mechanism when an axial pressure of corresponding height acts on the threaded rod. If the axial pressure that acts in the axial direction in such a way that the thread flanks, formed without an undercut, of the threaded rod and the internally threaded segment are pressed against each other, is sufficiently high, the internally threaded segment is displaced or positioned outwards in the radial direction due to the thread flanks oriented at an angle to the axial direction. The male thread of the threaded rod and the internal thread of the internally threaded segment are thus disengaged and the threaded rod can slip through in the axial direction. In this way, a quick positioning of the threaded rod in axial direction is possible.

On the whole, the invention allows the threaded rod to be quickly positioned in the one axial direction, while a pure axial displacement in the other, opposite axial direction is inhibited by the undercut and the threaded rod can only be moved in this direction by a screwing process. The invention allows the threaded rod to be advanced in the axial direction without screwing movement until a counterpressure exerted by the rod becomes too high. From this point on, further axial positioning can be achieved by a screwing process, whereby high forces can be transmitted to the rod. Loosening of the threads of the threaded rod and internally threaded segment is not possible in an advantageous manner due to the undercut and the instrument is secured.

As soon as the rod has reached the desired end position, it can be secured to the implant with a set screw or similar. To remove the instrument, the threaded rod has to be detached from the internally threaded segment by unscrewing until it is relieved of pressure. The threads of the threaded rod and the internally threaded segment can then be disengaged despite the undercut by actuating an unlocking device available with a special embodiment, i.e. with a pressure-relieved threaded rod. The threaded rod can then be retracted by means of pure axial positioning. It is a particular advantage of the invention that, in addition to largely fatigue-free work and time savings, since not the entire axial positioning has to be carried out by a screwing process, it is not possible to uncouple the two threads under high axial pressure load, so that injuries to surrounding structures or surgical staff can be avoided and prevented.

Advantageous designs of the invention are explained in more detail below.

The coupling unit is designed to couple the instrument to the implant. The implant is preferably a pedicle screw screwed into a vertebra of a spine. The coupling unit is preferably coupled to a pedicle screw head. For the purpose of coupling the instrument to the implant, the coupling unit can form or have an implant holder. Such an implant holder can include two or three opposing coupling arms. These are provided with a coupling structure at their respective proximal end. At least the proximal ends of the coupling arms can be spaced apart or spread apart in the radial direction, can be placed on an implant in the spaced state and coupled to an implant and fixedly arranged thereon by closing the proximal ends of the coupling arms.

The threaded rod can be designed for direct or indirect contact with a rod to be pressed into an implant. In the latter case, it may be connected to a rod pusher unit or a rod pusher element and contact and position/shift the rod via this. Preferably, the threaded rod and the rod pusher are coupled to each other in a rotatable manner around the longitudinal axis, so that rotations of the threaded rod around its longitudinal axis are not transmitted to the rod during screwing.

In one embodiment, the rod pusher unit can cooperate with the coupling arms of the coupling unit for example by passing the coupling arms through openings in the rod pusher unit so that the coupling arms are automatically closed or secured to the implant in the closed state when the rod pusher unit is positioned in the proximal direction.

The internally threaded segment is preferably designed in the form of a threaded shell with an internal thread or internal thread section facing the threaded rod. In the context of the invention, the instrument has at least one internally threaded segment. However, it is advantageous if it has two internally threaded segments opposite each other on both sides of the threaded rod, which are spaced from each other by an angle of 180° in the circumferential direction. It is also within the scope of the invention if the instrument has three or four internally threaded segments equally spaced from each other in the circumferential direction (in the case of three internally threaded segments, the angles are 120° each, in the case of four internally threaded segments, the angles are 90° each).

In one embodiment, a thread flank formed with an undercut may have a negative flank angle $\alpha$ inclined relative to a normal to the respective thread axis, preferably in a range from approx. $-10°$ to approx. $-1°$, more preferably from approx. $-8°$ to approx. $-2°$, more preferably from approx. $-6°$ to approx. $-3°$, even more preferred from approx. $-5°$ to approx. $-4°$. It is obvious that the flank angles of the threaded rod are matched to those of the internally threaded segment.

It is particularly advantageous if the flank angles of the threaded rod which are formed with an undercut are arranged distally and the flank angles of the threaded sleeve which are formed with an undercut are arranged proximally. In this case, it is not possible to position the threaded rod in the distal axial direction when the threads of threaded rod and internally threaded segment are in engagement with each other. Loosening the thread engagement by shifting the internally threaded segment radially outwards is not possible when the threaded rod is under pressure load, as the undercut blocks such a movement. The engaged threads are secured. However, if the threaded rod is relieved of the pressure load by partially loosening and unscrewing it, the thread engagement can be loosened despite the undercuts, resulting in a slight displacement of the threaded rod in the proximal axial direction.

In a further development of this design, the thread flanks each opposite a flank with undercut are formed with a positive flank angle $\beta$. In this way, the threaded rod can be positioned in the proximal axial direction even when the threads are in engagement, by applying a sufficiently high axial pressure to the threaded rod, wherein the internally threaded segment is forced outwards in the radial direction against the preload acting on it via the positive flank angle of the proximal flanks of the threaded rod and the distal flanks of the internally threaded segment, which act in the manner of an inclined plane.

In one embodiment, the internally threaded segment is accommodated in a housing. In particular, it can be preloaded toward the threaded rod by means of a spring, which spring is guided on or in the housing and supported outwards in radial direction.

In one embodiment of the invention, the instrument also has an unlocking device, preferably in the form of two unlocking elements. These can be arranged in particular in tangential direction on both sides of the internally threaded segment. They can also be positionable in radial direction by user actuation. The unlocking elements are preferably in contact with the internally threaded segment via an inclined plane. Like the internally threaded segments, they can be positioned radially in relation to the threaded rod. As a result of the radial inward preload of the internally threaded segments, i.e. toward the threaded rod, and their contact with it, the unlocking elements are preloaded in the radial outward direction. By positioning the unlocking unit radially inwards, i.e. toward the threaded rod and against the preload acting on the internally threaded segments, for example by user actuation, the threads of the threaded rod and the internally threaded segment can be disengaged. The prerequisite for this is that the previously described thread locking through the undercut can be unlocked by relieving the pressure on the threaded rod.

In a particular embodiment, the user of the instrument can be informed acoustically that the threaded rod is relieved of pressure. For this purpose, the threaded rod is frictionally inhibited in an axial movement in the proximal direction. This can be done in particular by an abutment of the threaded rod or a unit axially coupled to it, such as the coupling unit, with an axially fixed housing. Preferably, the frictional inhibition is dimensioned such that its axial displacement is prevented when the threaded rod is unscrewed from the internally threaded segment, so that the internally threaded segment is displaced radially outwards against its preload. If the threaded rod is sufficiently loosened and is not axially displaced by the rod pressed into the implant, the threads of the internally threaded segment snap into the next thread of the male thread after approximately one turn of the threaded rod, whereby an audible click indicates to the user that the threaded rod is pressure-relieved.

It is advantageous to turn in a set screw into the implant or pedicle screw if the threaded rod is hollow with a passage channel continuously extending in the axial direction. The passage channel is dimensioned such that the set screw as well as an instrument for screwing in the set screw fit through it.

It can also be said that the invention concerns an instrument mentioned above with a latching mechanism in an improved form with further safety features. In a starting position, prestressing elements, for example in the form of springs, can compress two internally threaded segments which are realized in the form of threaded shells, for instance. These can rest against an unlocking device, for example in the form of pushbuttons, with a lateral bevel and push them apart. The threaded shells and pushbuttons can be guided laterally in a housing. At the top and the bottom, they can be guided through boundary surfaces of the housing, for example.

When inserting the threaded rod, the threaded shells can spring back and then immediately grip it again. The thread form has an undercut. This means that the thread can be pushed through in one direction while it gets caught in the other direction. This has the advantage that the threaded rod connected to the rod pusher can be inserted by hand so far until the counterforce exerted by the rod becomes too large. From this point on, it is possible to screw, because the thread flanks get caught.

After the instrument has been placed on the implant, the threaded rod (as described above) can be pushed down by hand so far until the counter force from the rod becomes too large. The threaded rod can be released in any position due to the undercut thread used and the self-locking action of the thread and still holds its position. Then the screwing process can be continued and the rod be pressed completely into the tulip.

Since the latching mechanism has an undercut thread according to the invention, an uncoupling (a deflection) of the threads is not possible, especially under axial pressure, because a higher axial counterforce (of the rod) results in a stronger mutual engagement of the thread flanks. Furthermore, the pushbuttons are blocked, as a movement is not possible due to the blocked undercut thread being under load. In this way, the pushbuttons cannot be actuated by mistake.

A set screw can be screwed tight in the screw body through the rod persuader. It can hold the rod in the screw or tulip so that the rod persuader can be released and uncoupled. To release the blocked mechanism, it is sufficient to turn the threaded rod a few turns against the screw-in direction. An acoustic signal, for example in the form of a click, can inform the surgeon that the instrument is no longer under load and that he can safely retract the threaded rod by pressing the two push buttons together. The acoustic signal is provided as an additional safety feature. It can be generated, for example, by the fact that a frictional force for axial retraction of the threaded rod in the instrument is greater than a frictional force induced by friction in the thread directed in the opposite direction, whereby the threaded shells pretensioned toward the threaded rod, in particular pressed by springs, move outwards against the preload and the thread can slip through. An anew engagement of the thread is noticeable as a click.

The constructional design of the acoustic signal may be such that, in the case of two unlocking devices, the surgeon may necessarily have to actuate both in order to be able to retract the threaded rod. By actuating the pushbuttons, slopes of the unlocking devices and the thread shells may collide and push the thread shells apart so that the thread is out of engagement. Now the threaded rod can be pulled back again into the starting position, especially backwards or in the distal direction. If the surgeon does not want to pull back the threaded rod, but prefers to screw it back in a controlled manner, he can do so by directly or indirectly manually actuating the threaded shell and pressing it radially toward the threaded rod. This operation must then be carried out for as long as he wishes to screw back.

For example, the threaded shell can be pressed using a knob of a safety release device, which prevents the threaded shell from disengaging. This can be done either by increasing the spring force acting against the threaded shell or by pressing the knob against the threaded shell. Since in both cases disengaging is prevented, the thread cannot slip through and the instrument can be screwed back. It is important that, unlike unscrewing (moving backwards or in distal direction), the surgeon can always screw back without actuating the safety release when screwing in (moving forwards or in the proximal direction) as soon as the rod offers sufficient counterforce, since the thread flanks are pressed into one another by counterforce of the rod and cannot get uncoupled.

In another preferred embodiment, the rod pusher unit has a stop and the instrument has a locking element arranged in an axially fixed manner in relation to the coupling unit for interaction with the stop, which can be positioned in the radial direction relative to the threaded rod and is biased into engagement with the stop by a biasing element applying a radial force toward the threaded rod. In the following description, the prestressing element that preloads the locking element toward the threaded rod is referred to as the "first prestressing element" in order to distinguish it from any other prestressing elements of embodiments of the instrument. However, the term "first prestressing element" does not mean that the instrument must have a second prestressing element or further prestressing elements.

The longitudinal axes of the threaded rod and the rod pusher are coincident, in other words, they are arranged one behind the other in the axial direction. The stop, which according to the invention can be either on or in the threaded rod and/or on or in the rod pusher, can project outwards, especially in the radial direction. It is designed according to one embodiment of the invention in the form of a radial offset, a shoulder or a step. It is advantageous if it is fully circumferential, as this ensures unintentional loosening of the threaded rod regardless of its rotational positioning. The stop is preferably formed on the distal side of the male thread.

The advantage of this embodiment is that high contact forces can be exerted on a rod to be pressed into a tulip, on the one hand, due to the thread engagement between the threaded rod and the internally threaded segment with fine adjustment and, if necessary, self-locking of the thread. On the other hand, the instrument has a kind of quick adjustment which is effected by decoupling the thread engagement between the threaded rod and the internally threaded segment. The instrument does therefore not have to be tediously adjusted over the entire adjustment range by relative screwing action, but can be advanced and opened quickly, easily and without any effort by decoupling. A particular advantage is that, unlike with known instruments, complete loosening of these two components is safely and easily prevented by ensuring that the locking element is in engagement or comes into engagement with the stop due to its radial preload, despite the quick adjustment by decoupling the threaded rod and internally threaded segment. In this way, a kind of safety lock is formed. Complete disassembly is nevertheless possible quickly and easily by loosening the locking element from the engagement with the stop on the user's side. This ensures that complete disassembly is not accidental, but always intentional.

When using the instrument, the threaded rod can be quickly positioned in the axial direction by decoupling it from the internally threaded segment. The threaded rod can thus be advanced in axial direction without performing a screwing movement until a counterpressure exerted by the rod becomes too high. From this point on, further axial positioning can be achieved by means of a screwing process, whereby high forces can be transmitted to the rod. As soon as the rod has reached the desired end position, it can be secured to the implant with a set screw or the like. To remove the instrument, the threaded rod can first be detached by unscrewing it from the internally threaded segment until it is relieved of pressure. By uncoupling the male thread of the threaded rod from the internal thread of the internally threaded segment, the threaded rod can then be retracted by means of a pure axial positioning. According to the invention, however, this free axial positioning capability is limited by the stop of the threaded rod and the locking element being or coming into engagement with it. A particular advantage of the invention is that, in addition to largely fatigue-free work and time savings, since not the entire axial positioning does have to be done by screwing, it is not possible to unintentionally completely loosen or remove the threaded rod from the instrument.

One embodiment of the invention is characterized in that the outer diameter (maximum diameter) of the stop is smaller than the base diameter of the male thread. This ensures that engagement between the internally threaded segment and the stop is not possible. In this way, damage to the internal thread can be safely avoided. Furthermore, when the threaded rod is completely removed from the instrument, it can be avoided that the internally threaded segment comes into engagement with the stop, making disassembly difficult.

It is particularly advantageous if an axial unthreaded section is formed in the threaded rod with an outer diameter that is smaller than the base diameter of the male thread. The axial length of such a section can be greater than the axial length of the internal thread of the internally threaded segment according to one embodiment. The unthreaded section creates a kind of idle range in which the threaded rod can be turned relative to the internally threaded segment without feed in the axial direction. In this way, the instrument can be easily set on a pedicle screw and prepared for pressing in the rod. The unthreaded section can be formed particularly on the distal side of the male thread. A further embodiment of the invention provides that an unthreaded section is formed both distally and proximally.

One embodiment of the invention is characterized in that the instrument has an unlocking element which cooperates with the locking element. The locking element can be moved outwards in the radial direction, in particular by actuating the unlocking element on the user side, possibly against the preload applied by the first prestressing element, and can thus be able to be decoupled from the stop. The unlocking element can preferably be positioned in the radial direction relative to the threaded rod.

According to a further embodiment, the unlocking element may be accommodated in a housing. Within said housing, it can be pretensioned in particular by means of a spring as the first prestressing element in the direction away from the threaded rod, i.e. radially outwards. In a particular embodiment, this spring is arranged between the locking element and the unlocking element and braces these two elements against each other. A preload of the locking element toward the threaded rod can be effected by the unlocking element being able to cooperate with a stop formed in the housing, which forms a limitation for a movement of the unlocking element radially away from the threaded rod. In this way, the unlocking element forms a kind of floating bearing or seat for the locking element.

It is of particular advantage if the locking element has a contact surface for the threaded rod, with which it can slide in axial direction on the threaded rod while adjoining the head diameter (outer diameter) of the male thread, without coming into engagement with the male thread. In this way, a functional separation of the safety lock from the thread adjustment is achieved, which ensures particularly simple operation of the instrument. Furthermore, the locking element may have an inlet surface arranged in the manner of an inclined plane, i.e. oriented obliquely to the longitudinal axis of the threaded rod, for contact with the distal end of the threaded rod, which facilitates the insertion of the threaded rod into the instrument.

A further embodiment of the invention is characterized in that the internally threaded segment can be positioned in the radial direction relative to the threaded rod and is prestressed toward the threaded rod by a second prestressing element applying a radial force, with the internally threaded segment preferably being accommodated in a housing and preferably prestressed toward the threaded rod by means of a spring as a second prestressing element. The internally threaded segment can be engaged with or disengaged from the male thread of the threaded rod in particular by radial positioning. When the internally threaded segment is positioned in the radial direction to the threaded rod, hereinafter also referred to as the first position, the male thread of the threaded rod and the internal thread of the internally threaded segment are in engagement with each other. When the internally threaded segment is positioned radially away from the threaded rod, hereinafter also referred to as the second position, they are disengaged. In the second position, the threaded rod can therefore be freely positioned axially relative to the internally threaded segment, i.e. axially both in distal and proximal directions, in particular by action on the part of the user.

The internally threaded segment can be accommodated in particular in the housing in which also the locking element is accommodated and the unlocking element is mounted. In particular, it can be preloaded toward the threaded rod by means of a spring, which spring is guided on or in the housing and supported towards outside in radial direction.

One embodiment of the invention is characterized in that thread flanks of the threaded rod and thread flanks of the internally threaded segment, which face each other, are each formed with an undercut.

According to one embodiment of the invention, the locking element and the internally threaded segment are arranged on diametrically opposite sides of the threaded rod. The unlocking element can be positioned by user-side actuation in a first direction, especially in the radial direction towards the threaded rod, and in a second direction, especially in the radial direction away from the threaded rod. In this way, either the internal thread of the internally threaded segment can be unlocked from the male thread of the threaded rod or the locking element can be unlocked from the stop with a single unlocking element as user-side actuation unit. This is particularly user-friendly. In particular, when positioned in the first direction, the unlocking element can be moved away from the threaded rod against the radial force of the prestressing element and disengaged from its male thread, and when positioned in the second direction, the locking element can be moved away from the threaded rod against the radial force of the prestressing element and disengaged from its stop.

The following advantages in particular can be achieved by the invention:
  Two push buttons for intentional operation
  Undercut thread, self-locking thread
  The higher the force, the more secure the mechanism is against loosening Blocked pushbuttons on load, no inadvertent release possible Acoustic signal (click) if there is no load when turning back Switching option to be able to screw back further when free of load

BRIEF DESCRIPTION OF THE DRAWING FIGURES

Figure 2:
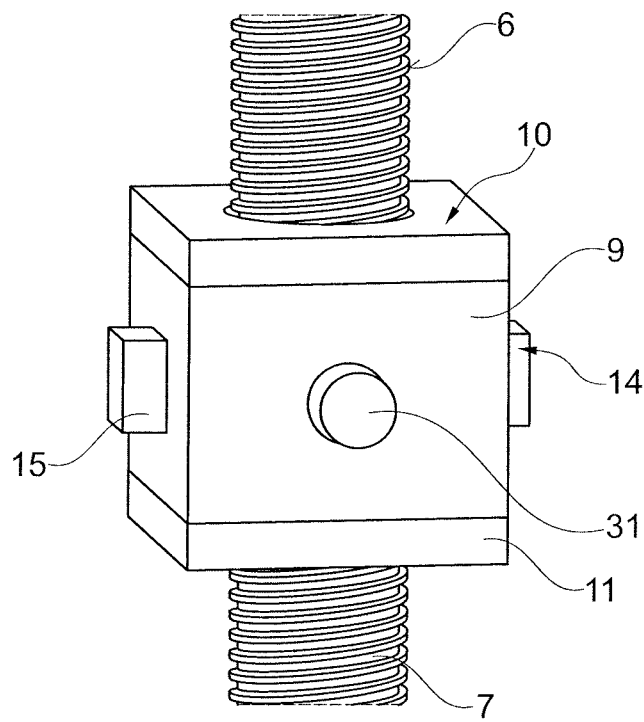
Figure 3:
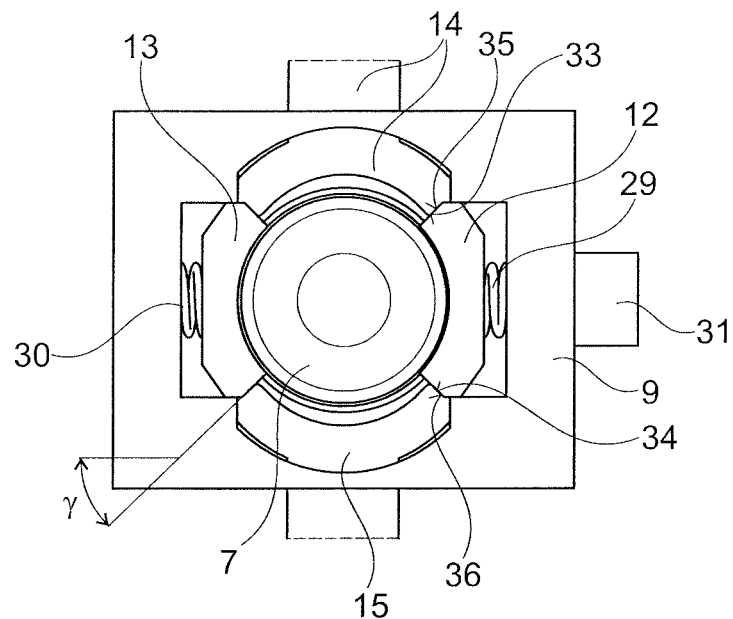
Figure 4:
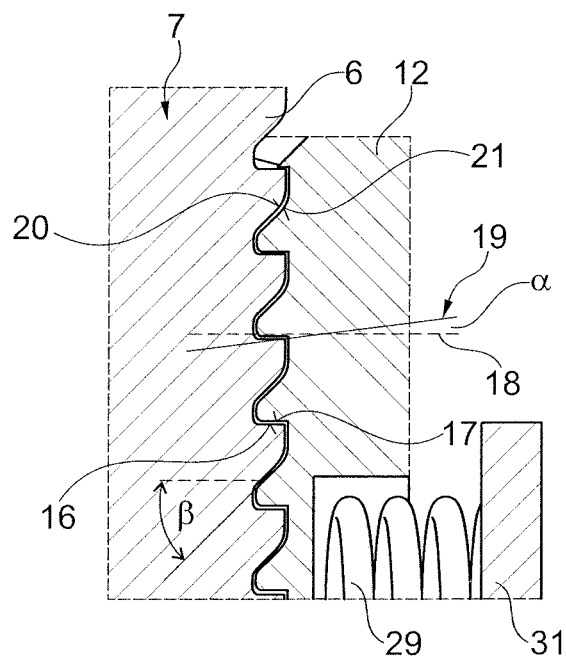
Figure 5:
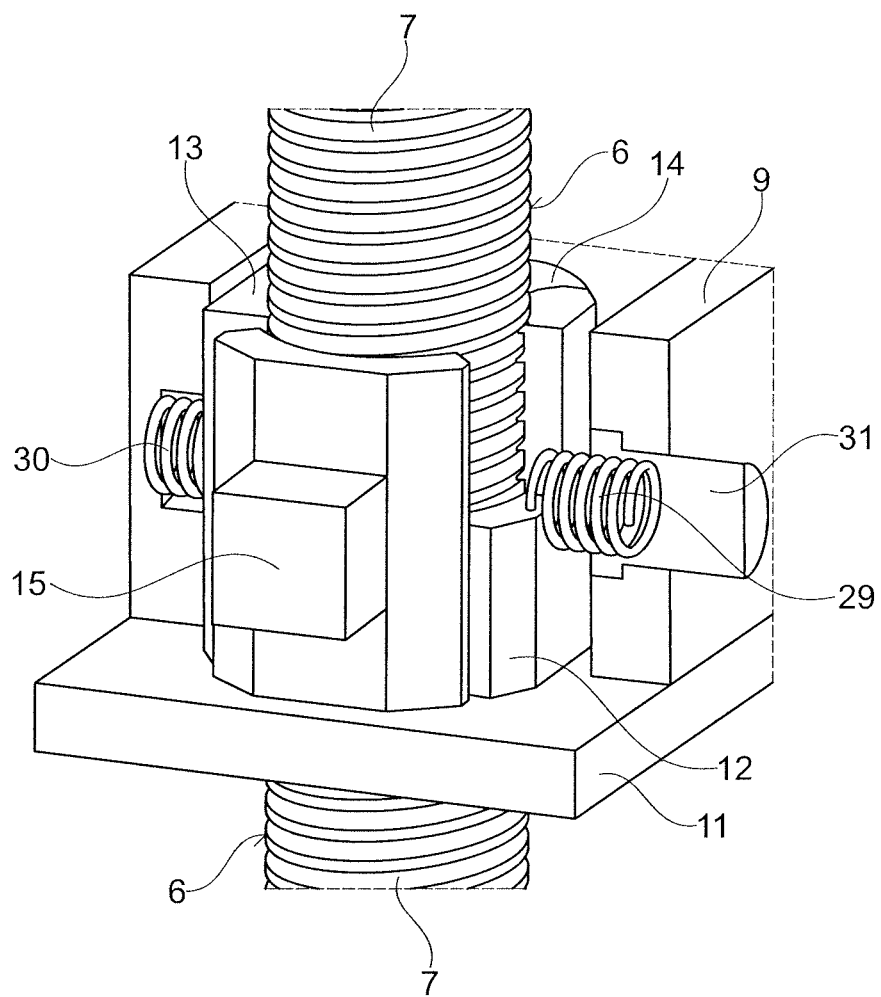
Figure 6:
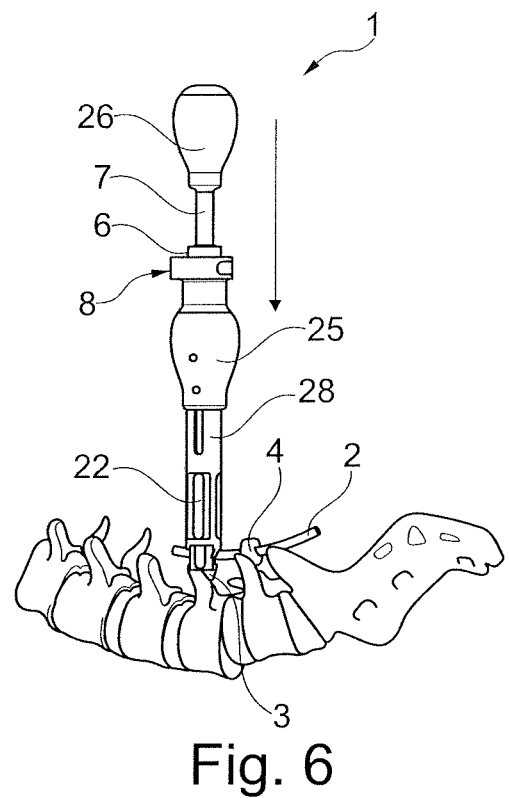
Figure 7:
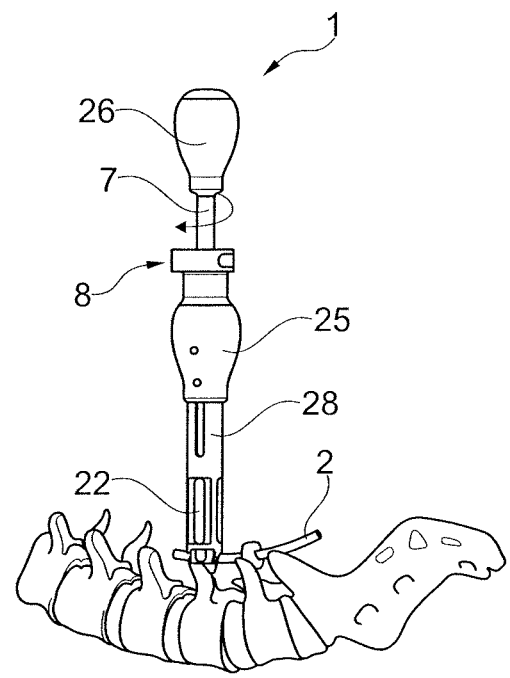
Figure 8:
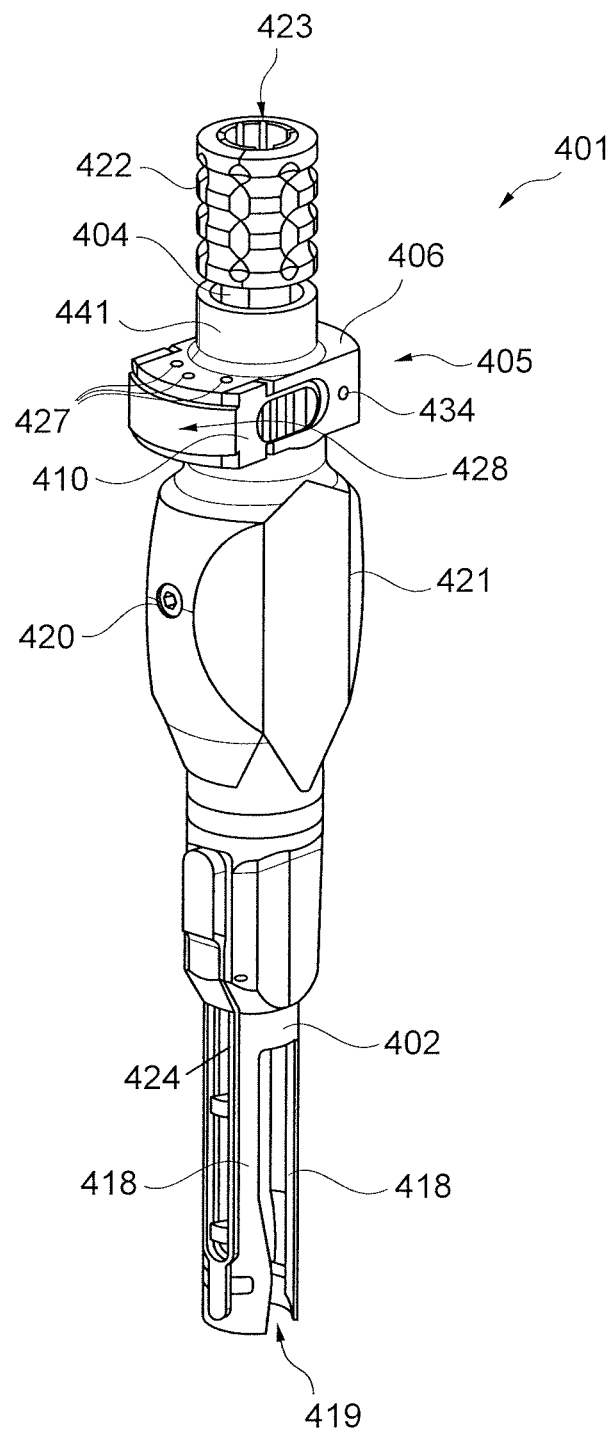
Figure 9:
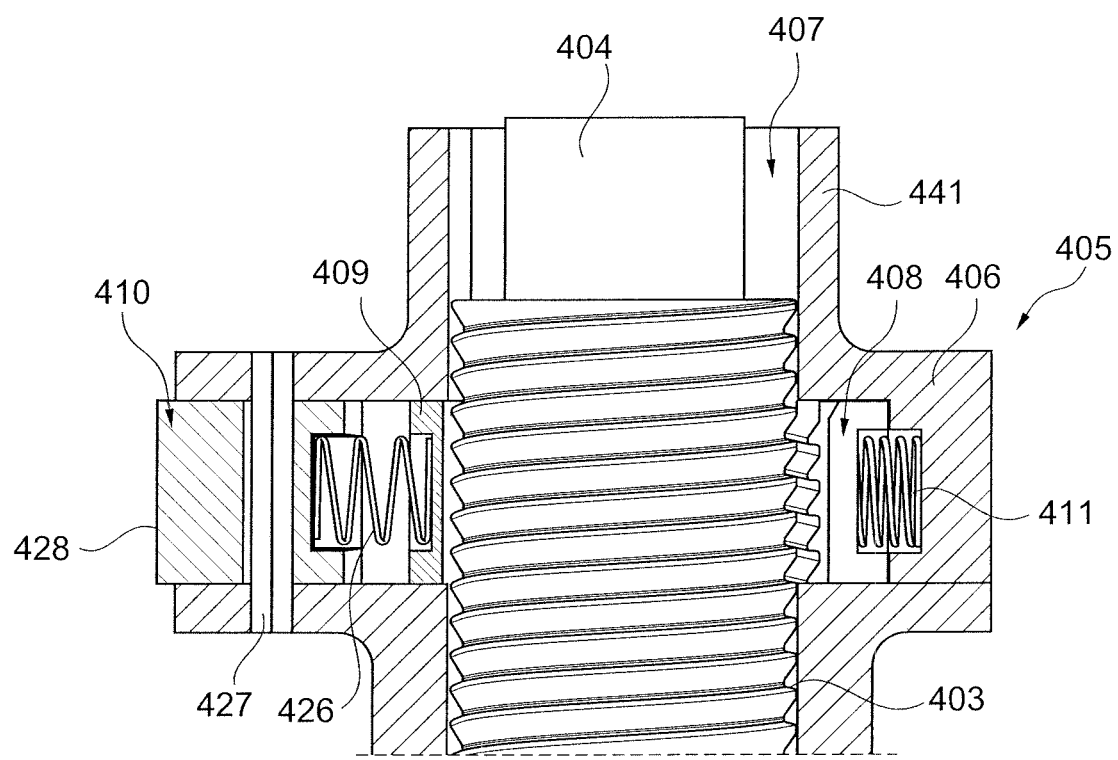
Figure 10:
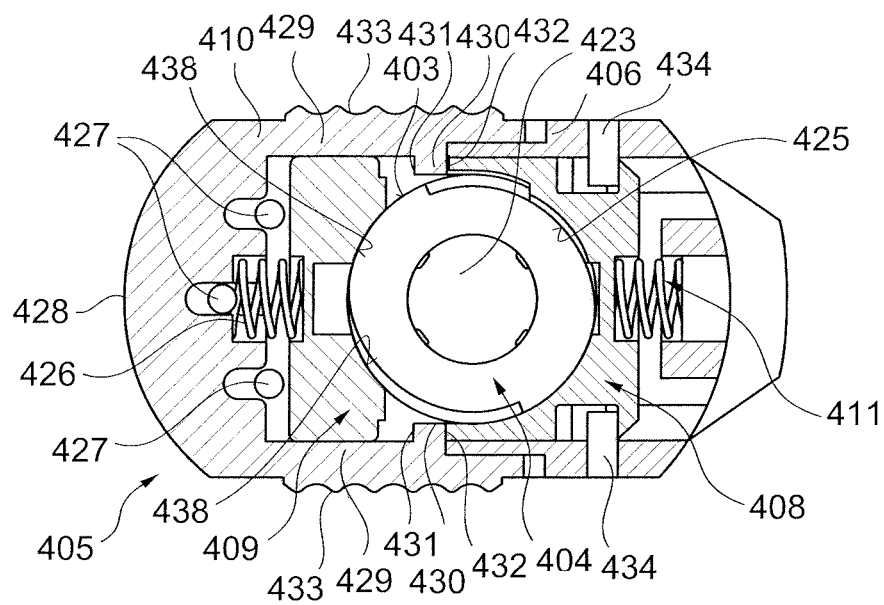
Figure 11:
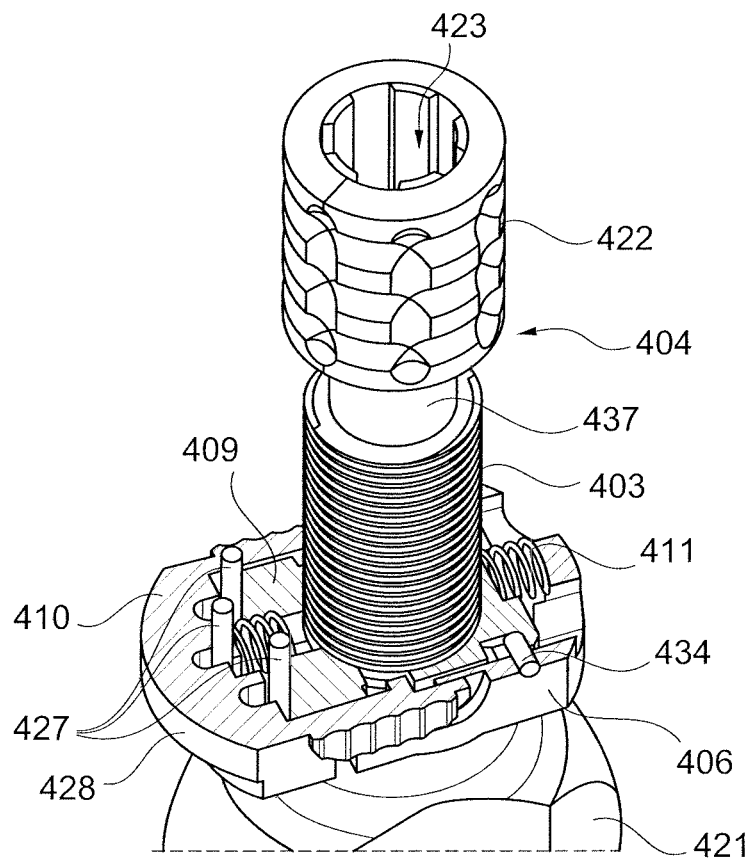
Figure 12:
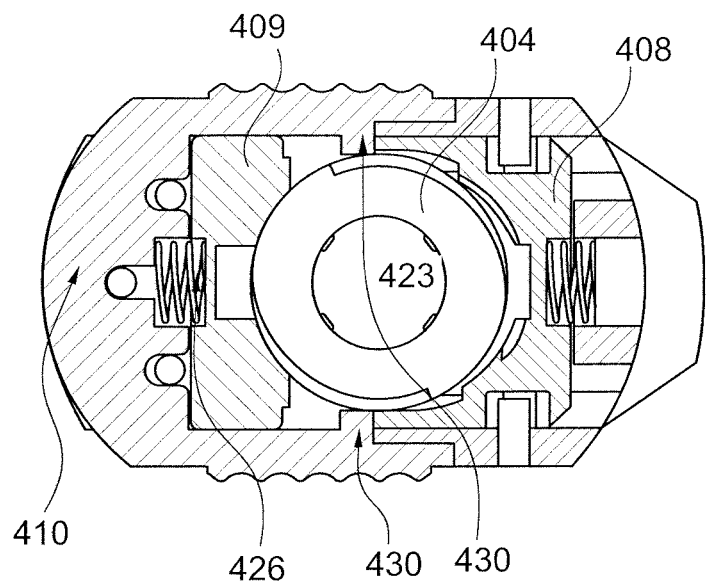
Figure 13:
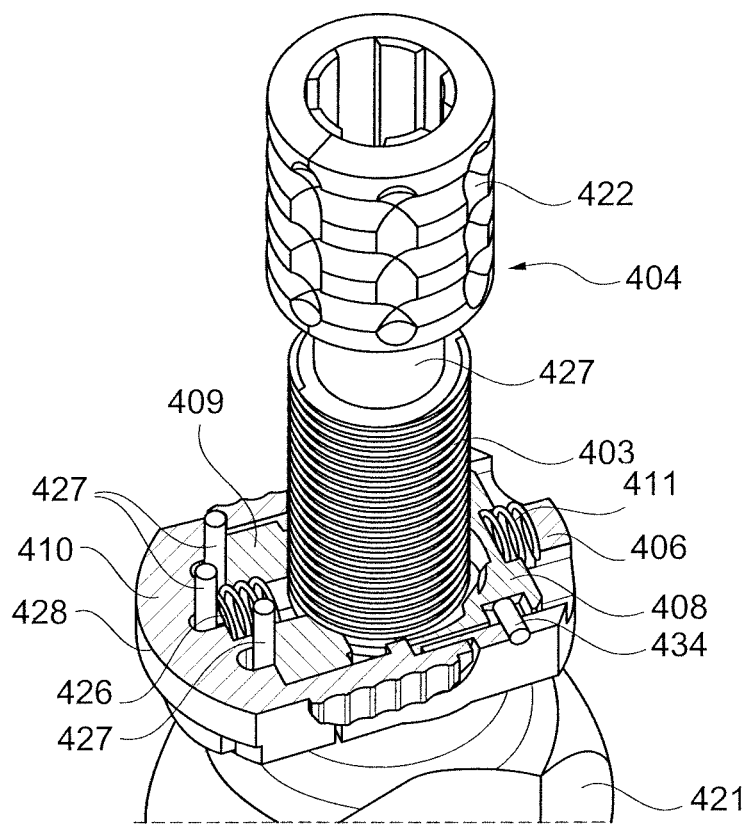
Figure 14:
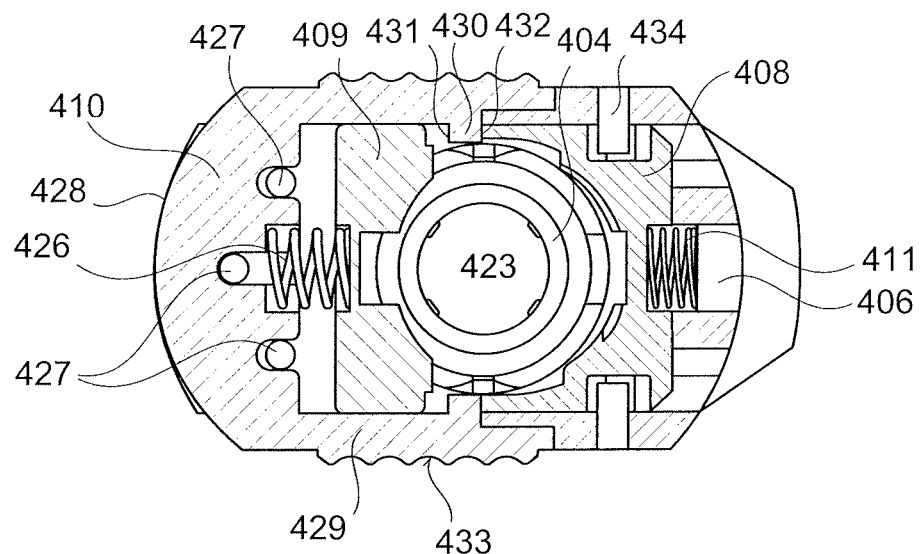
Figure 15:
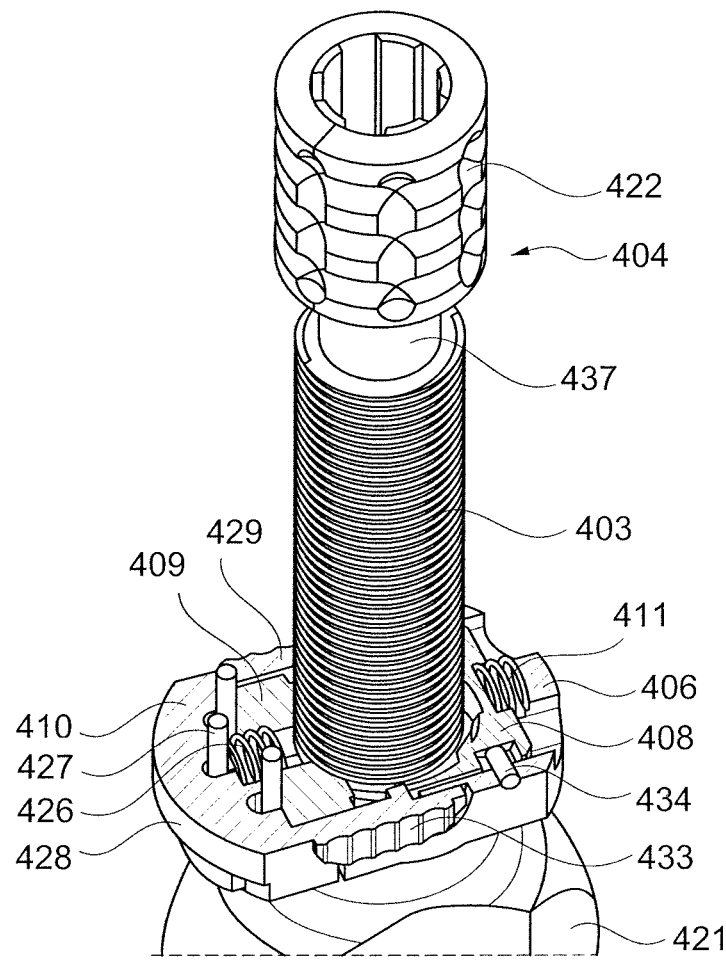
Figure 16:
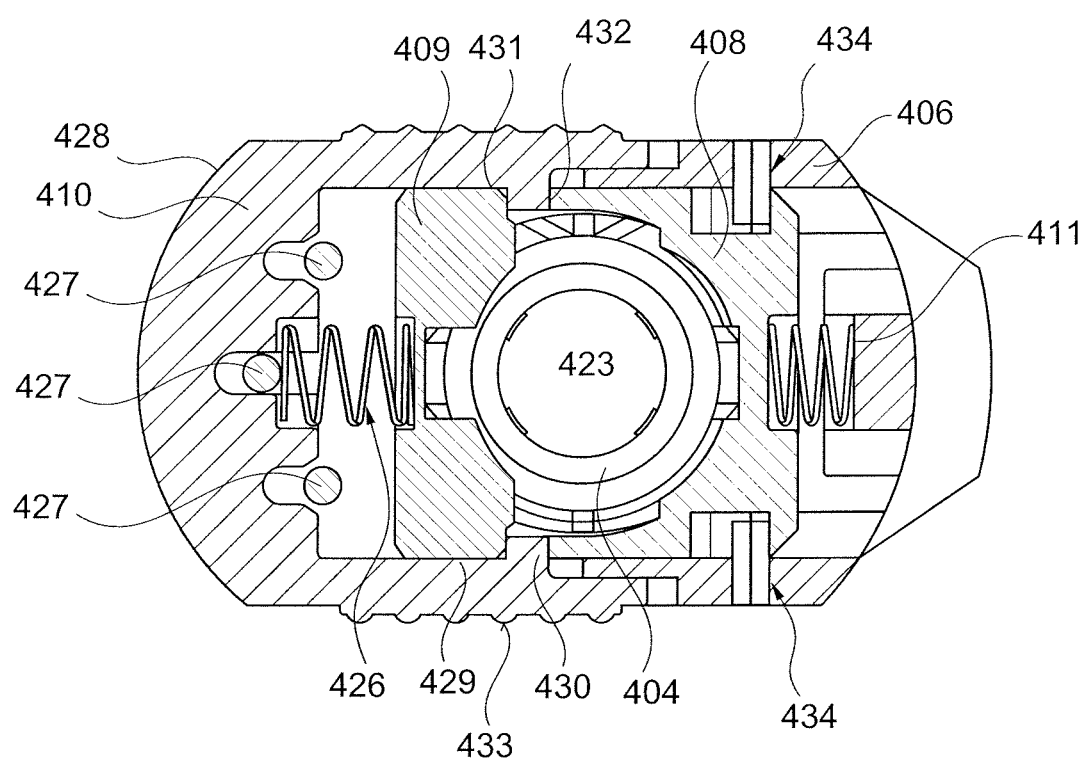
Figure 17:
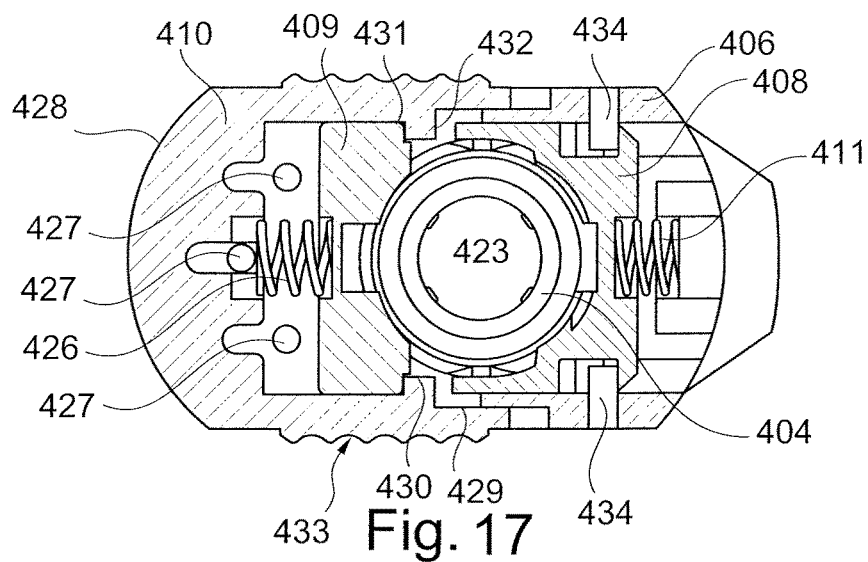
Figure 18:
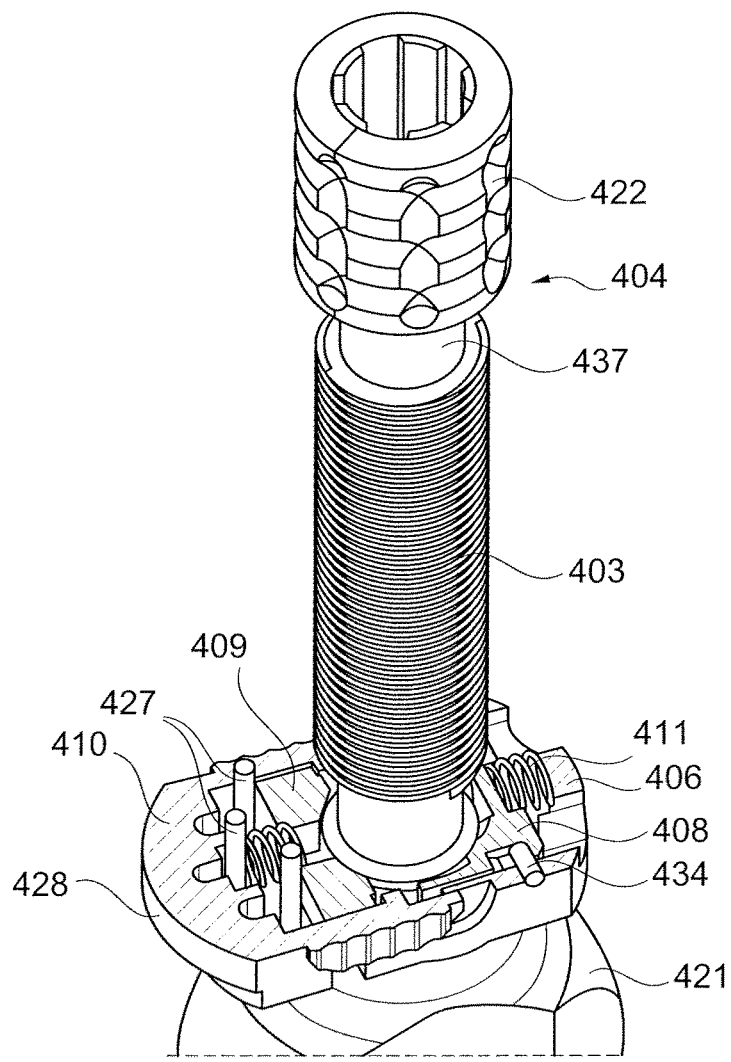
Figure 19:
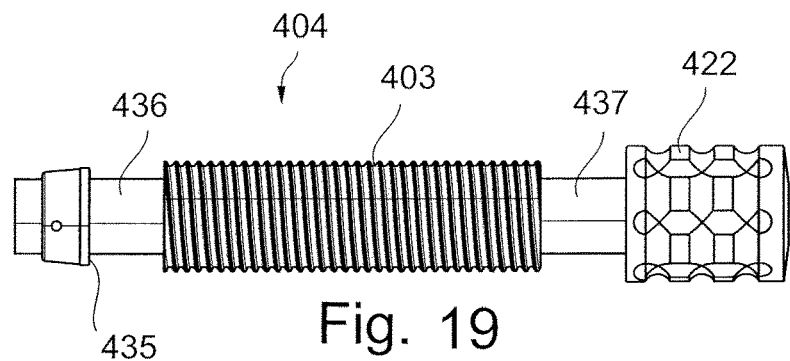
Figure 20:
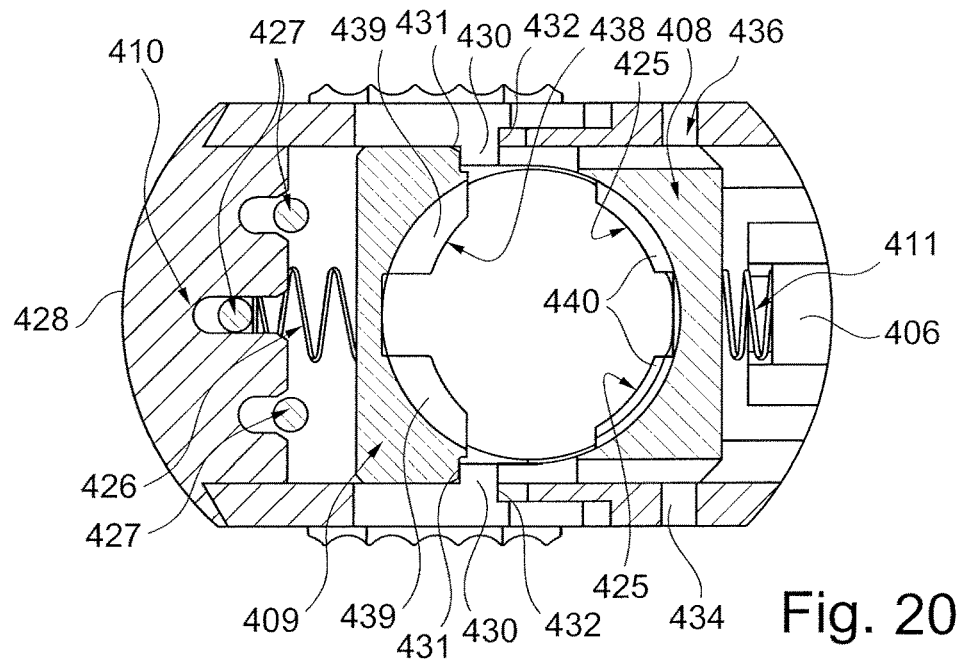
Figure 21:
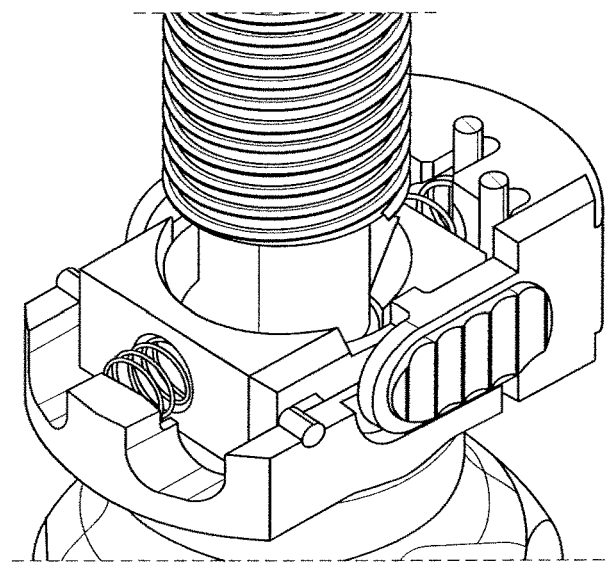
Figure 22:
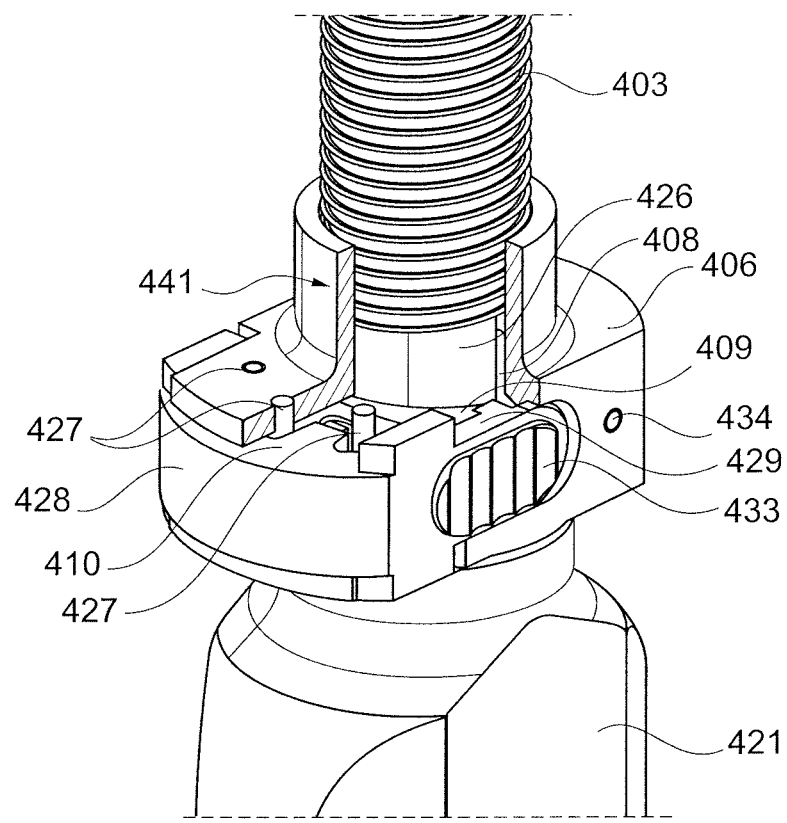
Figure 23:
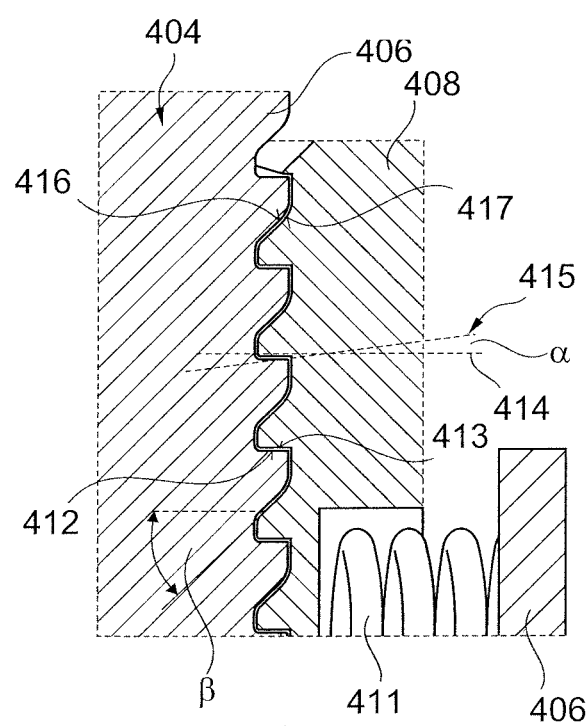

Further features and advantages of the present invention will be apparent from the following exemplary and non-restrictive description of the invention with the aid of Figures. These are only schematic in nature and merely serve to understand the invention. In the Figures:

FIG. 1 shows an instrument according to the invention in a perspective view,

FIG. 2 is a perspective view of a latching mechanism of the instrument of FIG. 1, FIG. 3 is a sectional view of the latching mechanism of FIG. 2 transverse to the axial direction, FIG. 4 shows a detail of the latching mechanism of FIG. 2 in a sectional view in axial direction, FIG. 5 is a partially exposed perspective view of the latching mechanism of FIG. 2, FIG. 6 is an illustration of the instrument when inserting a rod into a pedicle screw during a spinal surgery at a first point in time, FIG. 7 is an illustration of the instrument when inserting a rod into a pedicle screw during a spinal surgery at a second point in time, FIG. 8 shows an instrument according to the invention in a perspective view, FIG. 9 is a sectional view of a latching mechanism of the instrument of FIG. 8 in the direction of the longitudinal axis of the instrument, FIG. 10 is a sectional view of the latching mechanism of FIG. 8 transverse to the axial direction in a first functional position, FIG. 11 is a partially exposed perspective view of the latching mechanism of FIG. 9 in the first functional position, FIG. 12 is a sectional view of the latching mechanism of 6 FIG. 9 transverse to the axial direction in a second functional position, FIG. 13 is a partially exposed perspective view of the latching mechanism of FIG. 9 in the second functional position, FIG. 14 is a sectional view of the latching mechanism of FIG. 9 transverse to the axial direction in a third functional position, FIG. 15 is a partially exposed perspective view of the latching mechanism of FIG. 9 in the third functional position, FIG. 16 is a sectional view of the latching mechanism of FIG. 9 transverse to the axial direction in a fourth functional position, FIG. 17 is a sectional view of the latching mechanism of FIG. 9 transverse to the axial direction in a fifth functional position, FIG. 18 a partially exposed perspective view of the latching mechanism of FIG. 9 in the fifth functional position, FIG. 19 is a lateral view of a portion of the threaded rod, FIG. 20 is a top view of the mechanism of the instrument without threaded rod, FIG. 21 is a perspective view of the mechanism without housing, FIG. 22 is the view of FIG. 8 with partially exposed housing, and FIG. 23 is a partial section through the internal and male thread.

DETAILED DESCRIPTION

FIG. 1 shows an instrument 1 according to the invention for the relative positioning of and/or for guiding and/or inserting a rod 2 into a holder of an implant 3, here into a head 4 of a pedicle screw 3 in a perspective view. The instrument essentially comprises a coupling unit 5, a threaded rod 7 provided with a male thread 6 and positionable in the axial direction with respect to the coupling unit 5, and a latching mechanism 8 which is arranged in an axially fixed manner relative to the coupling unit 5.

The latching mechanism 8 is shown in FIGS. 2, 3, 4 and 5 together with a portion of the threaded rod 7. It essentially comprises a housing 9, a housing base 10, a housing cover 11, a first internally threaded segment 12, a second internally threaded segment 13, a first unlocking element 14 and a second unlocking element 15.

The first as well as the second internally threaded segment 12, 13 can each be positioned in radial direction with respect to the threaded rod 7 and are pretensioned in each case toward the threaded rod 7 by a prestressing element 29, 30 in the form of a compression spring 29, 30 which applies a radial force. Due to the capability of radial positioning, each of the two internally threaded segments 12, 13 can be engaged with or disengaged from the male thread 6 of the threaded rod 7 by shifting or placing it in the radial direction.

In particular FIG. 4 shows that thread flanks 16 of the thread rod 7 and thread flanks 17 of each internally threaded segment 12, 13, which face each other, are each formed with an undercut. To illustrate the undercut, FIG. 4 shows a normal 18 to the longitudinal axis of the threaded rod 7. Also drawn is a line 19 which overlaps the thread flanks 16, 17. A negative flank angle α extends between normal 18 and line 19. Each thread flank 20 opposite an undercut thread flank 16 of the male thread 6 of the threaded rod 7 is formed with a positive flank angle β. Likewise, each thread flank 21 opposite an undercut thread flank 17 of each internally threaded segment 12, 13 is formed with a positive flank angle β.

FIG. 1 shows that the coupling unit 5 has two opposing coupling arms 22, each of which is provided with a coupling structure 23 at its proximal end, for an at least axially fixed coupling of the instrument 1 to the head 4 of a pedicle screw 3. The coupling unit 5 is connected to a proximal handle element 25 by means of bolts or rivets 24 in a non-rotatably and axially fixed manner. The handle element 25, in turn, is connected to the housing 9 of the latching mechanism 8 in a non-rotatable and axially fixed manner.

FIG. 2 shows that the housing 9, the housing base 10 and the housing cover 11 are each designed with a through-opening in which the threaded rod 7 is arranged. The distal end of the threaded rod 7 is provided with a distal handle element 26 and on its part is essentially hollow-cylindrical with a passage channel 27 extending throughout it in the axial direction. The threaded rod 7 is axially fixed to a rod pusher 28 at its proximal end. The threaded rod 7 and the rod pusher 28 can be rotated relative to each other about the longitudinal axis of the threaded rod 7.

On the whole, it can be said that the coupling unit 5, the proximal handle element 25 and the housing 9, 10, 11 with the internally threaded segments 12, 13 and unlocking elements 14, 15 housed therein form a first unit of the instrument 1. Similarly, the threaded rod 7, the rod pusher 28 and the distal handle element 26 form a second unit of the instrument 1. The first unit and the second unit of the instrument are coupled together by an engagement of the male thread 6 of the threaded rod 7 in the internal threads of the internally threaded segments 12, 13.

FIGS. 3, 4 and 5 show that both internally threaded segments 12, 13 are inwardly pretensioned in the radial direction, i.e. toward the threaded rod 7, by means of a spring 29 and 30, respectively. The spring 29 is supported by an actuating element 31 which engages through a through-opening in the housing 9 and is received therein and supported in the radial direction towards outside. Similarly, the unlocking elements 14, 15 are arranged and held in through-openings in the housing 9.

In the circumferential direction, the internally threaded segment 12 is provided with an abutment surface 33, 34 on both sides. Both abutment surfaces are essentially designed to lie in a radial direction. The abutment surface 33 is in contact with a corresponding abutment surface 35 formed on the unlocking element 14. The abutment surface 34 is in contact with a corresponding abutment surface 36 formed on the unlocking element 15. Due to the circumferential extension of the internally threaded segment 12, the abutment surfaces 33, 34 are aligned at an angle γ oblique to the direction of movement of the internally threaded segment 12. Similarly, the abutment surfaces 35, 36 are obliquely aligned relative to the direction of movement of the respective unlocking elements 14, 15. It can therefore be said that the abutment surfaces 33, 34, 35, 36 form two inclined planes over which the internally threaded segment 12 is operatively connected to the unlocking elements 14, 15. The internally threaded segment 13 is designed accordingly and is operatively connected to the unlocking elements 14, 15 in corresponding manner.

The instrument 1 is used as follows: At the beginning of a procedure for pressing a rod 2 against a pedicle screw 3, the second unit consisting of distal handle element 26, threaded rod 7 and rod pusher 28 is pulled out in the distal direction from the first unit already described. In this state, the instrument 1 is arranged with the coupling structure 23 on the head 4 of the pedicle screw 3 and coupled thereto, whereby the rod 2 to be pressed in is placed between the two coupling arms 22.

The threaded rod 7 is then inserted into the instrument 1 in the proximally axial direction. This can be done with a pure axial movement without rotation of the threaded rod 7 about its longitudinal axis. In this process, the internally threaded segments 12, 13 spring back outwards in the radial direction, since the mutually contacting thread flanks 20, 21 without undercut each act like an inclined plane. As a result of the radial preload, the male thread 6 and the internal thread of the internally threaded segments 12, 13 slip back into each other again when an axial position is reached in which threads of the male thread 6 overlap with thread tips of the internal threads.

If the threads engage each other again, they "get caught" as a result of the undercut. On the whole, the inventive design of the threads brings about that the threaded rod 7 can be pushed without screwing movement through the internally threaded segments 12, 13 in one direction, namely in the present exemplary embodiment in the proximal direction, while a pure axial movement in the other direction (distal) is prevented. This has the advantage that the threaded rod 7 connected to the rod pusher 28 can be inserted by hand in the proximal direction until the counterforce exerted by the rod 2 on the rod pusher 28 becomes too large. Then a further infeed in the proximal direction is made by screwing the threaded rod 7 into the internal thread segments 12, 13. In the operations described above, the threaded rod 7 can be released in any position due to the undercut thread and the resulting self-locking effect and still retains its position.

Since the latching mechanism 8 has an undercut thread, any unintentional uncoupling of the male thread 6 from the internal threads of the internally threaded segments 12, 13, for example by unintentional spring deflection against the spring preload, is impossible, because a higher axial counter force on the rod 2 results in a stronger engagement of the thread flanks. Furthermore, the unlocking elements 14, 15 (pushbuttons) are blocked as a result of the undercut, since they cooperate via the abutment surfaces 33, 34, 35, 36 with the internally threaded segments 12, 13 which are not able to move due to the blocked undercut thread under load. Accidental unlocking is therefore not possible.

Once the rod 2 in the head 4 of the pedicle screw 3 has reached its intended position, a set screw (not shown in the Figures) is screwed through the passage channel 27 of the threaded rod 7. It holds the rod 2 in the screw 3 or in the head 4, so that the instrument according to the invention can now be released and uncoupled. To do this, the threaded rod 7 has first to be rotated a few turns against the screw-in direction.

The threaded rod 7 is frictionally inhibited in an axial movement in the proximal direction by itself and/or the rod pusher 28 being in frictional contact with an axially fixed element of the instrument 1, for example with the proximal handle element 25. The frictional inhibition is dimensioned in such a way that when the threaded rod 7 is unscrewed from the internally threaded segments 12, 13 without additional pressure load by the rod 2, axial displacement of the threaded rod 7 is prevented. As a result, the internally threaded segments 12, 13 are displaced outwards in the radial direction against the preload of the springs 29, 30. When the threaded rod 7 is sufficiently loosened and there is no pressure exerted on it by the rod 2 (which is the case when the rod 2 is secured by means of the set screw), the threads of the internally threaded segments 12, 13 snap into place in the next thread of their male thread 6 after approximately one turn of the threaded rod 7, whereby an audible click indicates to the user that the threaded rod 7 is relieved of pressure and he can safely unlock the threaded rod 7 by pressing the two unlocking elements 14, 15 together and pull it back in the axial direction.

For unlocking, the operator must necessarily actuate both unlocking elements 14, 15 in the described exemplary embodiment in order to be able to retract the threaded rod 7 with a pure axial movement. By actuating the unlocking elements 14, 15, the abutment surfaces 33, 34, 35, 36 abut each other and push the internally threaded segments 12, 13 outwards in the radial direction, whereby the threads are disengaged from each other. Now the threaded rod 7 can be pulled into the starting position by means of a purely axial movement. If the surgeon does not wish to pull back the threaded rod 7, but rather to screw it back in a controlled manner, he can do so by actuating the operating element 31. The latter must remain activated as long as he wants to screw back. The pressure on the actuating element 31 prevents the internally threaded segments 12, 13 from moving radially outwards, in this example by pressure load on the springs 29, 30, which increases their spring force. The thread cannot slip through and the threaded rod 7 can be screwed back. In contrast to unscrewing (move distally backwards), the surgeon can screw back at any point in time without actuating the actuating element 31 when screwing in (move proximally forward), as the rod 2 then exerts a sufficient counterforce on the threaded rod 7, whereby the thread flanks 16, 17 are pressed into one another as a result of the undercut and the threaded rod 7 cannot be decoupled from the internally threaded segments 12, 13.

FIG. 8 shows an instrument 401 according to the invention for the relative positioning and/or the guiding and/or inserting of a rod (not shown in the Figures) into a holder of an implant (not shown either), such as into a head of a pedicle screw, in a perspective view. The instrument 401 essentially comprises a coupling unit 402, a threaded rod 404 provided with a male thread 403 and positionable in the axial direction in relation to the coupling unit 402, and a latching mechanism 405 arranged in an axially fixed manner relative to the coupling unit 402.

The latching mechanism 405 together with a portion of the threaded rod 404 is shown in an enlarged manner in FIG. 9, among others. It essentially has a housing 406 with a through-opening 407 extending in the axial direction, an internally threaded segment 408, a locking element 409 and an unlocking element 410. The housing 406 has a cylindrical guide 441 by means of which the threaded rod 404 is guided and positioned relative to the housing 406 and the units accommodated and supported therein.

The internally threaded segment 408 can be positioned in radial direction relative to the threaded rod 404 and is pretensioned toward the threaded rod 404 by a prestressing element 411 (second prestressing element) in the form of a compression spring 411 which applies a radial force. Due to the capability of radial positioning, the internally threaded segment 408 can be engaged with or disengaged from the male thread 403 of the threaded rod 404 by moving or placing it in the radial direction.

Thread flanks 412 of the threaded rod 404 and thread flanks 413 of the internally threaded segment 408, which face each other, each are formed with an undercut. To illustrate the undercut, a normal 414 to the longitudinal axis of the threaded rod 404 is shown. Also drawn is a line 415 which overlaps the thread flanks 412, 413. A negative flank angle α extends between the normal 414 and the line 415. Each thread flank 416 opposite an undercut thread flank 412 of the male thread 403 of the threaded rod 404 is formed with a positive flank angle β. Likewise, each thread flank 417 opposite an undercut thread flank 413 of the internally threaded segment 408 is formed with a positive flank angle β.

FIG. 8 shows that the coupling unit 402 has two opposing coupling arms 418, each of which is provided with a coupling structure 419 at its distal end, for an at least axially fixed coupling of the instrument 401 to the head of a pedicle screw. The coupling unit 402 is connected to a distal handle element 421 by means of screws or rivets 420 in a non-rotatable and axially fixed manner. The handle element 421, in turn, is connected to the housing 406 of the latching mechanism 405 in a non-rotatable and axially fixed manner.

FIG. 9 shows that the threaded rod 404 is located in the through-opening 407 of the housing 406. The threaded rod 404 is provided at its proximal end with a proximal handle element (not shown in the Figures), which is coupled to the threaded rod 404 in a non-rotatable manner via a holder 422, and in turn has a substantially hollow-cylindrical design comprising a passage channel 423 extending throughout in the axial direction. At its distal end, the threaded rod 404 is fixed to a rod pusher 424 in an axially fixed manner. The threaded rod 404 and the rod pusher 424 can be rotated relative to each other about the longitudinal axis of the threaded rod 404.

On the whole, it can be said that the coupling unit 402, the distal handle element 421 and the housing 406 with the internally threaded segment 408, the locking element 409, which can also be referred to as a locking latch, and the unlocking element 410 form a first unit of the instrument 401. Similarly, the threaded rod 404, the rod pusher 24 and the proximal handle element form a second unit of the instrument 401. The first unit and the second unit of the instrument are coupled together by engagement of the male thread 403 of the threaded rod 404 in the internal thread 425 of the internally threaded segment 408.

The internally threaded segment 408 is preloaded inwards in the radial direction, i.e. toward the threaded rod 407 by means of the spring 411. The latter is supported radially outside on the housing 406. The locking element 408 is pretensioned against the threaded rod 404 in the radial direction by means of a compression spring 426 (first prestressing element). In a state of rest, the compression spring 426 is supported radially on the outside on a middle pin of three guide pins 427. These support an unlocking element 410 which can be positioned in the radial direction in housing 406, the radially outer end of which projects out of housing 406 and is designed as operating knob 428. In the above state of rest, the unlocking element 410 is located radially spaced from the threaded rod 404 (FIG. 10). If the operating knob 428 is actuated, i.e. shifted radially toward the threaded rod 404, the compression spring 426 comes into contact with it and is supported by it. The unlocking element 410 has two lateral arms 429 which extend tangentially to the threaded rod 404 on both sides of knob 428. On each of their sides facing the threaded rod 404, they have a stop pin 430 with a first stop face 431 and a second stop face 432. The first stop face 431 is designed to cooperate with the locking element 409, and the second stop face 432 is designed to cooperate with the internally threaded segment 408. A handle structure 433 is formed on the outer sides of each arm 429 (see for example in FIG. 10). FIG. 20 shows that the internally threaded segment 408 is guided in the housing 406 with pins 434.

The radially inner end of the locking element 409 is provided with two contact surfaces 438 and sliding surfaces 439 arranged axially above. The contact surfaces 438 are designed in such a way that the locking element 409 can rest on the outer shell surface (outer diameter) of the male thread 403 of the threaded rod 404 and slide thereon in the axial direction without coming into meshing engagement with the male thread 403. The sliding surfaces 439 facilitate the axial insertion of the threaded rod 404.

Since the threaded rod 404 usually has to be retracted several times during a surgery, for example to press a rod into several pedicle screws, the invention provides that the instrument 401 will not unintentionally disassemble. For this purpose, the threaded rod 404 is designed with a stop 435 (see FIG. 19 in particular). Distally of the male thread 403, there is formed an unthreaded section 436. Its diameter is smaller than the base diameter (inner diameter) of the male thread 403. The stop 435 is located distally to the non-threaded section 436. A second unthreaded section 437, which is without function in the present example, is formed to be proximal to the male thread 403.

The instrument 401 is used as follows:

First, the threaded rod 404 is inserted into the through-opening 407 of the housing 406. In this process, its distal end comes into contact with the sliding surfaces 439 of the locking element 409, whereby the locking element 409 is pushed radially outwards against the tension of the spring 411. The same applies to the internally threaded segment 408, which has similar sliding surfaces 440. The threaded rod 404 is now inserted in the through-opening 407 of the housing 406 and is in thread engagement with the internally threaded segment 408.

With the threaded rod 404 mounted, the instrument 401 is coupled with the pedicle screw in a starting situation. At the beginning of a procedure for pressing a rod against a pedicle screw, the second unit consisting of proximal handle element 422, threaded rod 404 and rod pusher 424 is pulled out in the proximal direction from the first unit already described. In this state, the instrument 401 is placed with the coupling structure 419 on the head of the pedicle screw and coupled thereto, with the rod to be pressed in being placed between the two coupling arms 418.

The threaded rod 404 is then inserted into the instrument 401 in the distally axial direction. Due to the positive flank angles β described above, the threaded rod 404 can be pushed by hand in the distal direction (downwards) by pure axial displacement. In this process, the internally threaded segment 408 is pressed radially outwards by the male thread 403 due to the positive flank angles β until the threaded rod 404 and the internally threaded segment 408 are out of engagement. The threaded rod can be moved axially until it or the rod pusher 424 rests against the pedicle screw. The thread engagement is restored as a result of the radial preload by the spring 411. Further axial positioning is now achieved by turning the threaded rod 404 and unscrewing it from the internally threaded segment 408.

If the threads engage with each other again, they "get caught" as a result of the undercut. On the whole, the undercut of the thread has the effect that the threaded rod 404 can be pushed through the housing in one direction, namely in the present exemplary embodiment in the distal direction, without any screw movement (with displacement of the internally threaded segment 408 radially outwards), while a pure axial movement in the other direction (proximally) is prevented. This has the advantage that the threaded rod 404 connected to the rod pusher 424 can be inserted manually in distal direction until the counterforce exerted by the rod on the rod pusher 424 becomes too large. Then a further infeed in the proximal direction is made by screwing in the threaded rod 404. In the operations described above, the threaded rod 404 can be released in any position due to the undercut thread and the resulting self-locking effect and still retains its position.

Since the latching mechanism 402 has an undercut thread, unintentional uncoupling of the male thread 403 from the internal thread of the internally threaded segment 408, for example by unintentional spring deflection against the spring preload, is impossible, because a higher axial counter force on the rod leads to a stronger engagement of the thread flanks. Furthermore, as a result of the undercut, the unlocking element 410 is blocked by a contact between the stop pin 430 and the stop faces 431, as it interacts with the internally threaded segment 8, whose movement is not possible due to the blocked undercut thread under load. Accidental unlocking is therefore not possible.

Once the rod has reached its intended position in the head of the pedicle screw by screwing the threaded rod 404 relative to the internally threaded segment 408, a set screw not shown in the Figures is tightened through the passage channel 423 of the threaded rod 404. It holds the rod in the screw or in the head, so that the instrument 401 can now be released and uncoupled. To do this, the threaded rod 404 has first to be rotated a few turns against the screw-in direction.

The threaded rod 404 is frictionally inhibited in the distal direction during an axial movement by itself and/or the rod pusher 424 being in frictional contact with an axially fixed element of the instrument 401, for example with the distal handle element 421. The frictional inhibition is dimensioned in such a way that an axial displacement of the threaded rod 404 is prevented when the threaded rod 404 is unscrewed from the internally threaded segment 408 without additional pressure load by the rod. As a result, the internally threaded segment 408 is displaced radially outwards against the preload of the spring 411. When the threaded rod 404 is sufficiently loosened and no more pressure is exerted by the rod (which is the case when the rod is secured by the set screw), the threads of the internally threaded segment 408 snap in place in the next thread of the male thread 403 after approximately one turn of the threaded rod 404, whereby an audible click indicates to the user that the threaded rod 404 is relieved of pressure and he can safely unlock the threaded rod 404 and retract it in axial direction by pressing the unlocking element 410, 428.

For unlocking, the operator must press the button 428 of the unlocking element 410 in the exemplary embodiment described in order to be able to retract the threaded rod 404 with a pure axial movement. The state when button 428 is pressed to unlock the threads is shown in FIGS. 12 and 13. By pressing the button 428, the actuating element 410 moves radially towards the threaded rod 404. Its stop pins 430 come into contact with the stop faces 432, so that the internally threaded segment 408 is pushed radially outwards away from the threaded rod 404 against the radial tension of the spring 411. In this way, the threads are disengaged. The threaded rod 404 can then be retracted into the starting position, i.e. in the proximal direction, by means of a purely axial movement.

However, the threaded rod 404 can be retracted due to the disassembly safety device according to the invention only until the locking element 409 comes into contact with the stop 435 of the threaded rod 404. The radially inward pretensioning of the locking element 409 by means of the spring 426 supported on the actuating element continuously forces the locking element 409 toward the threaded rod 404. In this process, its contact surfaces 438 slide off the outer diameter of the male thread 403 until the threaded rod is relatively positioned in the axial direction such that the locking element 409 overlaps with the unthreaded section 436. Due to its radial preload, the locking element 409 snaps radially inwards (virtually into the unthreaded section) and comes into contact with the stop 435 during further axial movement of the threaded rod 404. Then, the threaded rod cannot continue to move axially in the proximal direction, so that the instrument 401 is secured against unintentional complete disassembly of the threaded rod 404. The pretensioned spring 426 from the previous step favors safe snapping. Even if the button 428 is now released (see FIG. 16) the mechanism due to the continuous preload of the spring 426 is adjusted in such a way that the locking element 409 continues to engage in the unthreaded section 436, is in contact with the stop 435 of the threaded rod 404 and unintentional disassembly is prevented. FIG. 16 also shows the purpose of the pins 434: To prevent the internally threaded segment 408 from engaging in the unthreaded section 436 when the button 426 is released, it is held back radially on the outside by the pins 434.

After having retracted the threaded rod 404, the instrument 401 can be placed on another pedicle screw and the application is repeated as described above until the rod has been pressed into all pedicle screws and fixed. The application cycles occurring during an operation are shown in FIGS. 10 to 16.

After the end of the surgery, the instrument 1 can be disassembled for cleaning despite the disassembly safety device. To this end, the actuating element 10 is pulled radially outwards, i.e. away from the threaded rod 4, by the ribbed handle structures 33 provided on the side for this purpose. This causes the stop pins 30 to come into contact with the stop faces 31 of the locking element 9 and, with continuous radial positioning, the locking element 9 to move radially outwards until it detaches from the stop 35 of the threaded rod 4. The threaded rod 4 is then fully released and can be completely removed from the housing 6 by pure axial movement.

Since the male thread 403 has a larger diameter than the unthreaded section 436, the internally threaded segment 408 cannot snap in place in the undercut.

The invention claimed is:

1. An instrument for guiding a rod into a head of a pedicle screw, the instrument comprising:
   a coupling unit for coupling the instrument to the head of the pedicle screw,
   a threaded rod provided with a male thread and first thread flanks, the threaded rod being positionable in an axial direction relative to the coupling unit, and
   at least one internally threaded segment comprising second thread flanks and arranged in an axially fixed manner relative to the coupling unit, the at least one internally threaded segment positionable in a radial direction relative to the threaded rod and prestressed toward the threaded rod by a prestressing element applying a radial force,
   wherein the internally threaded segment can be brought into engagement with, and disengaged from, the male thread of the threaded rod by radial positioning,
   wherein the first thread flanks of the threaded rod and the second thread flanks of the internally threaded segment face each other, and are each formed with an undercut, and
   wherein at least one unlocking element is arranged in a tangential direction of the at least one internally threaded segment and is positionable in the radial direction by user-side actuation.

2. The instrument according to claim 1, wherein the first and second thread flanks formed with an undercut have a negative flank angle α inclined relative to a normal to a respective thread axis, said angel α being in a range approximately −10° to approximately −1°.

3. The instrument according to claim 1, wherein the flank angle α of the threaded rod is arranged distally and the flank angle α of the at least one internally threaded segment is arranged proximally.

4. The instrument according to claim 1, wherein the at least one internally threaded segment is received in a housing and is prestressed toward the threaded rod by a spring.

5. The instrument according to claim 1, wherein the at least one internally threaded segment comprises two internally threaded segments that are arranged radially opposite one another on both sides of the threaded rod.

6. The instrument according to claim 1, wherein the threaded rod is frictionally inhibited during an axial movement in a proximal direction.

7. The instrument according to claim 6, wherein, when the threaded rod is unscrewed from the internally threaded segment it is displaced outwards in the radial direction against its preload.

8. The instrument according to claim 1, wherein the threaded rod is hollow with a passage channel continuously extending in the axial direction.

9. The instrument according to claim 1, further comprising a rod pushing unit with a stop and a locking element arranged in a axially fixed manner relative to a latch that cooperates with the stop, which can be positioned in the radial direction with respect to the threaded rod and is prestressed toward the threaded rod into engagement with the stop by the prestressing element applying the radial force.

10. The instrument according to claim 9, further comprising an unlocking element disposed around the at least one internally threaded segment or around the locking element and capable of displacing the at least one internally threaded segment and/or the locking element in the radial direction.

11. The instrument according to claim 10, wherein the unlocking element has at least one stop pin that moves the at least one internally threaded segment or the locking element outwards in the radial direction by user-side actuation.

12. The instrument according to claim 9, wherein an outer diameter of the stop is smaller than a base diameter of the male thread.

13. The instrument according to claim 9, wherein the locking element has a smooth surface facing the threaded rod.

14. An instrument for guiding a rod into a head of a pedicle screw, the instrument comprising:
   a coupling unit for coupling the instrument to the head of the pedicle screw,
   a threaded rod provided with a male thread and first thread flanks, the threaded rod being positionable in an axial direction relative to the coupling unit, and
   at least one internally threaded segment comprising second thread flanks and arranged in an axially fixed manner relative to the coupling unit, the at least one internally threaded segment positionable in a radial direction relative to the threaded rod and prestressed toward the threaded rod by a prestressing element applying a radial force,
   wherein the internally threaded segment can be brought into engagement with, and disengaged from, the male thread of the threaded rod by radial positioning, and
   wherein the first thread flanks of the threaded rod and the second thread flanks of the internally threaded segment face each other, and are each formed with an undercut,
   the instrument further comprising two unlocking elements arranged in a tangential direction on both sides of the at least one internally threaded segment and positionable in the radial direction by user-side actuation.

15. The instrument according to claim 14, wherein each of the unlocking elements is in contact with the at least one internally threaded segment via an inclined plane.

\* \* \* \* \*